United States Patent [19]

Jacobs et al.

[11] 4,359,428

[45] Nov. 16, 1982

[54] PREPARATION OF FLUORINATED ANTHRANILIC ACID AND ANTHRANILONITRILE

[75] Inventors: Peter Jacobs, Gruenstadt; Heinz-Guenter Oeser, Dirmstein, both of Fed. Rep. of Germany

[73] Assignee: BASF Aktiengesellschaft, Ludwigshafen, Fed. Rep. of Germany

[21] Appl. No.: 318,588

[22] Filed: Nov. 5, 1981

[30] Foreign Application Priority Data

Nov. 28, 1980 [DE] Fed. Rep. of Germany ....... 3044904

[51] Int. Cl.³ .................. C07C 121/78; C07C 101/58
[52] U.S. Cl. ................................. 260/465 E; 562/456
[58] Field of Search ..................... 260/465 E; 562/456

[56] References Cited

U.S. PATENT DOCUMENTS

| | | | |
|---|---|---|---|
| 3,291,790 | 12/1966 | Strube | 260/239.3 |
| 3,374,262 | 3/1968 | Seefelder et al. | 260/465 E |
| 3,783,142 | 1/1974 | Bakke et al. | 260/465 E |
| 4,145,364 | 3/1979 | Mulvey et al. | 260/465 E X |
| 4,178,304 | 12/1979 | Litvishkov et al. | 260/465 E |

Primary Examiner—Dolph H. Torrence
Attorney, Agent, or Firm—John H. Shurtleff

[57] ABSTRACT

Fluorinated anthranilic acid and anthranilonitrile, and a novel process for their preparation by reacting 2,6-difluorobenzonitrile with ammonia and, if the acid is required, hydrolyzing the resulting 6-fluoroanthranilonitrile with a basic compound.

The two novel end products are valuable intermediates for the preparation of compounds which are useful for controlling various animal pests and plant pests.

14 Claims, No Drawings

PREPARATION OF FLUORINATED ANTHRANILIC ACID AND ANTHRANILONITRILE

The present invention relates to C-fluorinated anthranilic acid and anthranilonitrile, and to a novel process for their preparation by reacting 2,6-difluorobenzonitrile with ammonia and, if the acid is required, hydrolyzing the resulting 6-fluoroanthranilonitrile with a basic compound.

Houben-Weyl, Methoden der Organischen Chemie, volume 5/3, pages 409–415, discloses that fluorine can be introduced in various ways into aromatic compounds, its introduction being difficult in non-substituted aromatics, whilst the yield is better if the aromatics are appropriately substituted by activating groups, such as the nitro group, or by chlorine atoms or fluorine atoms already present. Houben-Weyl shows that the ease of introduction of fluorine varies with the existing substitution and that a precise prediction concerning introduction of fluorine, and position of the resulting fluorine substituents, is difficult.

We have found that 6-fluoroanthranilic acid and its nitrile, of the formula

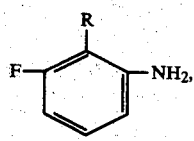
                                    I where R is —COOH or —CN respectively, are obtained in an advantageous manner when (a) 2,6-difluorobenzonitrile of the formula

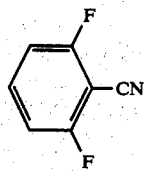
                                    II is reacted with ammonia and thereafter, if the acid is desired, (b) the resulting 6-fluoroanthranilonitrile of the formula

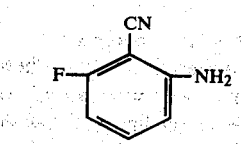
                                    III is reacted with a basic compound.

Further, we have found the novel anthranilic acid derivative of the formula III.

The reaction can be represented by the equations:

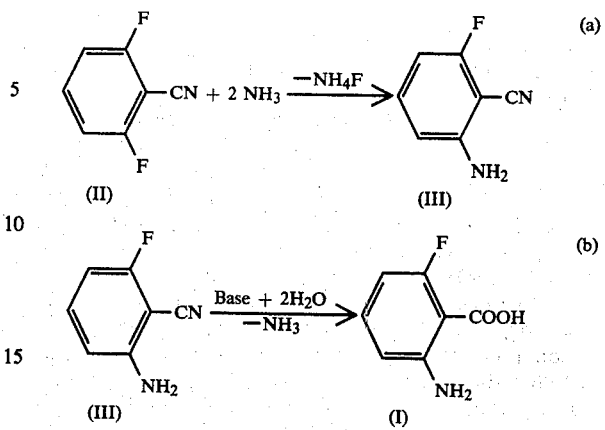

Compared to the prior art, the novel process gives 6-fluoroanthranilic acid and 6-fluoro-2-aminobenzonitrile simply and economically, in good yield and high purity. These advantageous results are surprising. It was to be expected that in the process according to the invention the formation of, for example,

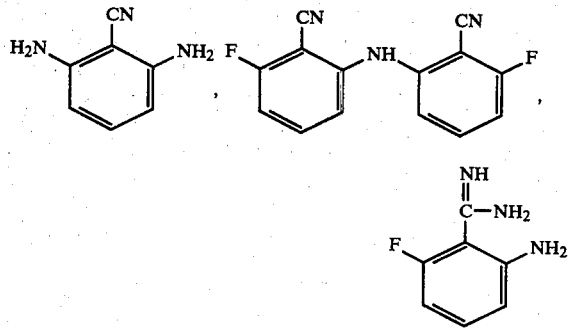

and their secondary products would result in only low yields of the end product I, and in the formation of inhomogeneous mixtures.

The starting material II can be prepared by conventional methods, for example by reacting 2,6-dichlorobenzonitrile with potassium fluoride by the method described in German Laid-Open Application DOS No. 2,803,259. In step (a), ammonia can be reacted with the starting material II in stoichiometric amount or in excess, preferably in a ratio of from 2 to 10, especially from 2 to 5, moles of ammonia per mole of starting material II. The ammonia can be used in gaseous form, or as an aqueous ammonia solution, advantageously of from 10 to 25 percent strength by weight, or, particularly advantageously, as liquid ammonia.

Reaction (a) is in general carried out at from 0° 1 to 200° C., advantageously from 50° to 150° C., especially from 70° to 120° C., under atmospheric or superatmospheric pressure, advantageously under the autogenous reaction pressure, continuously or batchwise.

To carry out the reaction, a mixture of the starting material II, with or without a solvent (for example an alkanol, eg. ethanol), and ammonia is kept at the reaction temperature for from half an hour to 11 hours. The end product is then isolated by conventional means, for example where necessary adding a suitable solvent, such as a halohydrocarbon, eg. methylene chloride, filtering, washing and drying the organic phase formed, and then distilling it.

The hydrolysis of compound III to give the end product I where R=COOH is as a rule carried out in an alkaline medium, using an alkaline earth metal compound or alkali metal compound, preferably in an aqueous solution, advantageously of from 10 to 50 percent strength by weight, of an alkaline earth metal hydroxide or alkali metal hydroxide. Amongst these, sodium hydroxide solution and potassium hydroxide solution are preferred. For example, a mixture containing from 5 to 30 percent by weight of end product III in such a solution is employed, and hydrolysis is advantageously effected at a pH of from 7 to 14, preferably from 8 to 13, and at from 0° to 150° C., preferably from 15° to 30° C., for from 6 to 15 hours. It is advantageous to add an alcohol, in general an alkanol of, advantageously, from 1 to 6 carbon atoms, preferably in an amount of from 2 to 10 percent by weight, especially of from 4 to 8 percent by weight, based on the amount of water.

The reaction can be carried out as follows: a mixture of compound III, aqueous alkali metal hydroxide solution and alcohol is kept at the hydrolysis temperature for from half an hour to 9 hours. The end product is then isolated by conventional means, for example acidifying to pH 3–4, filtering off and washing the solid or extracting the aqueous phase, for example with a suitable solvent such as methylene chloride, and distilling the extract.

The two end products I are valuable intermediates for the preparation of compounds which are useful for controlling various animal pests and plant pests. For example, the compounds where R=COOH can be subjected to the following reaction:

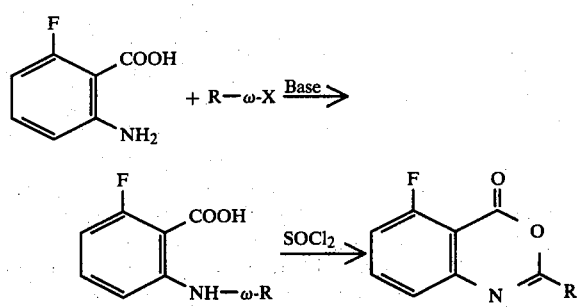

where X=halogen, valuable active ingredients being obtained.

In the Examples which follow, parts are by weight.

EXAMPLE 1

2-Amino-6-fluoro-benzonitrile 50 parts of 2,6-difluorobenzonitrile and 40 parts by volume of ammonia are stirred for 10 hours at 100° C. in a closed vessel. The reaction mixture is taken up in methylene chloride, the solid is filtered off, the organic phase is extracted three times by shaking with water and is dried over sodium sulfate, the solvent is stripped off and the residue is dried under reduced pressure. 48 parts (98.1% of theory) of 2-amino-6-fluoro-benzonitrile, of solidification point 125°–128° C., are obtained.

IR (KBr): 3450, 3360 (NH$_2$) and 2215 cm$^{-1}$ (CN)

$^1$H-NMR (CDCl$_3$):=6.45 (s, 2H, NH$_2$), 6.35–6.74 (m, 2H, aromatic), 7.19–7.49 (m, 1H, aromatic).

EXAMPLE 2

1,000 parts of 2,6-difluorobenzonitrile, 1,500 parts by volume of tetrahydrofuran and 800 parts by volume of ammonia are stirred for 10 hours at 100° C. in a closed vessel. The mixture is cooled to room temperature, the solid is filtered off and washed with tetrahydrofuran, and the organic phase is freed from solvent under reduced pressure. The residue is dried under reduced pressure. 972 parts (99% of theory) of 2-amino-6-fluorobenzonitrile, of solidification point 127° C., are obtained.

EXAMPLE 3

6-Fluoroanthranilic acid 56 parts of 2-amino-6-fluoro-benzonitrile, 33 parts of sodium hydroxide, 250 parts of water and 20 parts by volume of ethanol are refluxed for 8 hours. The pH is then brought to 3–4 with 20 percent strength by weight aqueous sulfuric acid and the precipitate formed is filtered off, washed with water and dried. The aqueous phase is extracted with methylene chloride, the solvent is stripped off under reduced pressure and the residue is dried, also under reduced pressure. In this way, a total of 58 parts of 6-fluoroanthranilic acid (90.9% of theory), of solidification point 165°–167° C., is obtained.

We claim:

1. A process for the preparation of 6-fluoroanthranilic acid or its nitrile, of the formula

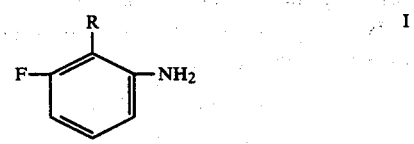

where R is —COOH or —CN respectively, wherein
(a) 2,6-difluorobenzonitrile of the formula

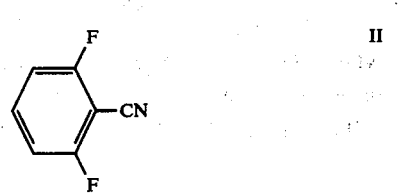

is reacted with ammonia and thereafter, if the acid is desired,
(b) the resulting 6-fluoroanthranilonitrile of the formula

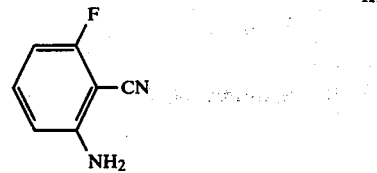

is reacted with a basic compound.

2. A process as claimed in claim 1, wherein the reaction in step (a) is carried out with from 2 to 10 moles of ammonium per mole of starting material II.

3. A process as claimed in claim 1, wherein the reaction in step (a) is carried out at from 0° to 200° C.

4. A process as claimed in claim 1, wherein the reaction in step (a) is carried out at from 50° to 150° C.

5. A process as claimed in claim 1, wherein the reaction in step (a) is carried out at from 70° to 120° C.

6. A process as claimed in claim 1, wherein the reaction in stage (b) is carried out at a pH of from 7 to 14.

7. A process as claimed in claim 1, wherein the reaction in stage (b) is carried out at from 0° to 150° C.

8. A process as claimed in claim 1, wherein the reaction in stage (b) is carried out at from 15° to 30° C.

9. A process for the preparation of the 6-fluoroanthranilonitrile of the formula

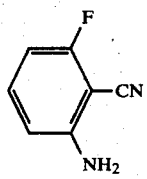

which comprises:
reacting 2,6-difluorobenzonitrile with ammonia at a temperature of from 0° to 200° C.

10. A process as claimed in claim 9 using from 2 to 10 moles of ammonia per mole of the starting benzonitrile.

11. A process as claimed in claim 10 wherein the reaction is carried out at from 50° to 150° C.

12. A process as claimed in claim 10 wherein the reaction is carried out at from 70° to 120° C.

13. A process for the preparation of 6-fluoroanthranilic acid of the formula

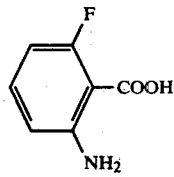

which comprises:
reacting the 6-fluoroanthranilonitrile of the formula

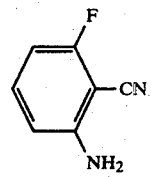

with a basic compound at a pH of from 7 to 14 and at a temperature of from 0° to 150° C.

14. A process as claimed in claim 13 wherein the reaction is carried out at from 15° to 30° C.

* * * * *